United States Patent [19]

Chambers

[11] Patent Number: 4,474,973

[45] Date of Patent: Oct. 2, 1984

[54] ACIDIC MIXED OXIDE CATALYTIC DEALKYLATION TO PRODUCE 1,4-BUTANEDIOL AND TETRAHYDROFURAN

[75] Inventor: Gregory R. Chambers, Rexford, N.Y.

[73] Assignee: General Electric Company, Schenectady, N.Y.

[21] Appl. No.: 491,127

[22] Filed: May 3, 1983

[51] Int. Cl.³ .................. C07C 27/00; C07C 29/00; C07D 307/08
[52] U.S. Cl. .................................. 549/509; 568/866
[58] Field of Search ..................... 549/509; 568/866

[56] References Cited

U.S. PATENT DOCUMENTS

| | | | |
|---|---|---|---|
| 3,467,679 | 9/1969 | Rogers | 549/509 |
| 4,136,099 | 1/1979 | Smith | 549/509 |
| 4,156,685 | 5/1979 | Tanabe et al. | 549/508 |
| 4,254,290 | 3/1981 | Chambers et al. | 568/866 |
| 4,287,127 | 9/1981 | Harris et al. | 549/509 |

FOREIGN PATENT DOCUMENTS 18163 9/1980 European Pat. Off.
7301075 5/1970 Japan.

*Primary Examiner*—Richard Raymond
*Attorney, Agent, or Firm*—Leo I. MaLossi; James C. Davis, Jr.; James Magee, Jr.

[57] ABSTRACT

A coproduct continuous dealkylation process is described in which 4-t-butoxy-n-butanol is contacted with acidic silica-alumina catalyst at temperatures in the 160°–200° C. range (reactor wall temperature) in the liquid hourly space velocity regime of 2:0 to 6:0 liter/liter catalyst/hr. to produce in a single reactor a mixture in which the ultimate product of conversion of the 4-t-butoxy-n-butanol is 1,4-butanediol (1,4-diol) and tetrahydrofuran (THF) present in a preselected ratio (mole %) of 1,4-diol to THF ranging from 7:3 to 3:7. The 1,4-diol produced is useful in the preparation of polyesters, e.g. polybutylene terephthalates, and THF is a useful intermediate in the manufacture of certain chemicals and plastics.

8 Claims, No Drawings

ACIDIC MIXED OXIDE CATALYTIC DEALKYLATION TO PRODUCE 1,4-BUTANEDIOL AND TETRAHYDROFURAN

BACKGROUND OF THE INVENTION

This invention relates to the coproduction of 1,4-butanediol (1,4-diol) and tetrahydrofuran (THF).

U.S. Pat. No. 4,136,099—Smith discloses the production of THF from 1,4-diol using tungsten oxide catalyst to effectuate the dehydration. Japanese Pat. No. 73 01 075 utilizes silica-alumina catalyst in a batch process to convert 1,4-diol to THF. The patent to Chambers, et al. (U.S. Pat. No. 4,254,290) discloses the use of a solid acidic silica-alumina composition for the highly selective conversion of 4-t-butoxy-n-butan-1-ol to 1,4-diol at temperatures in the 100°–140° C. range. In U.S. Pat. No. 4,156,685—Tanabe, et al., a complicated process is disclosed which interconnects separate reaction zones for the production of 1,4-diol in one reaction zone and THF in a second reaction zone. The starting material is an acetate ester of 1,4-diol and a solid acid catalyst is stated to be useful in the process.

Commercial catalysts used herein are referred to by trade name (i.e. Dowex, Amberlyst) or manufacturer.

DESCRIPTION OF THE INVENTION

The process of this invention comprises continuously contacting solid acidic silica-alumina catalyst with 4-t-butoxy-n-butanol (1,4-ether) alone, or in feedstock containing at least about 70 mole percent 1,4-ether, at temperatures (i.e. reaction tube wall temperature) in the 160°–200° C. range in the liquid hourly space velocity (LHSV) regime of 2.0 to 6.0 liter/liter catalyst/hr to produce a mixture in which the ultimate product of conversion of the 4-t-butoxy-n-butanol is 1,4-diol and THF present in a pre-selected ratio (mole %) of 1,4-diol to THF in the range of from 7:3 to 3:7 all in a single reactor. The preferred space velocity range is 3.0–5.0 and the preferred operating wall temperature is in the range of 180°–200° C.

In accordance with this invention, the following reactions are carried out in a single reactor by use of process parameters and catalyst system discussed above:

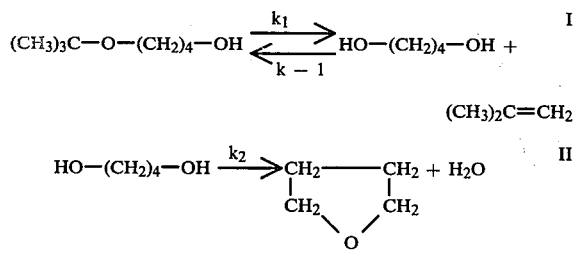

Side reactions, such as the formation of 1,4-di-t-butoxy-n-butane and t-butyl alcohol (by hydration of isobutene), also occur, but are not shown.

One of the most difficult problems faced in developing the capability for coproducing 1,4-diol and THF in a single reactor resides in the need to simultaneously cope with two reactions (above) having independently acting reaction rates ($k_1$ and $k_2$), one of which ($k_1$) is reversible. What was needed was to be able to set $k_1$ at a high level to minimize distillation costs and reactor size but at the same time to find a way to vary $k_2$ (i.e. the THF level) independently of $k_1$. As will be developed herein, successful execution of this objective has been made possible by determining both the right catalyst material and the right operating parameters for that catalyst material. Thus, by the practice of this invention as described and claimed herein 1,4-diol and THF can be coproduced in a single reactor in a predetermined ratio or high conversion and high reaction rate.

MANNER AND PROCESS OF MAKING AND USING THE INVENTION

The commercial demand for 1,4-diol and THF fluctuates. In order to accommodate this fluctuation, it is of economic advantage to be able to shift the ratio of 1,4-diol to THF to a preselected value on demand. This invention enables this desired alteration of product ratio in a simple, but highly effective, manner.

Because of the high selectivity exhibited by solid acidic silica-alumina catalyst in forming 1,4-diol from 4-t-butoxy-n-butanol in the substantial absence of cyclic ethers in Chambers, et al., it appeared improbable that this catalyst material would also function as a selective catalyst in this same system for the coproduction of 1,4-diol and THF in a single reactor in useful ratios.

One approach considered instead of the above was the use of small amounts of homogeneous strong acid catalysts (e.g. phosphoric or sulfuric acid) blended with the feedstock. Another approach involved the impregnation of heterogeneous catalysts, such as silica-alumina, with small amounts of strong acid catalyst.

Promising catalysts selected on the basis of the above premises and others were investigated in batch tests conducted using relatively pure 4-t-butoxy-n-butanol (1,4-ether) obtained by distillation (to avoid complications in catalyst response that could result from a feedstock mix). These catalysts were tested for activity and selectivity in the coproduction of 1,4-diol and THF in a single reactor. The results of these batch catalyst studies are presented in Table I to follow.

In each test, a small amount of transetherification to give 1,4-di-t-butoxy-n-butane was observed. In a typical batch test, 4.0 g 99+% pure 1,4-ether was placed in a 25 ml 2-neck round-bottom flask fitted with a water cooled reflux condenser, magnetic stirrer and nitrogen inlet. The catalyst (0.100 g) was added and the mix stirred at the desired temperature in an oil bath. Analysis was done on a $6' \times \frac{1}{8}''$, 10% Carbowax 20M on 100/120 Chromosorb W column. The column was held at 50° C. for 4 minutes, followed by a programmed temperature rise from 50° to 220° C. at 10° C./minute.

TABLE I

| Catalyst | Temp (°C.) | Time (h) | THF[a] | 1,4-Dicap[e] | 1,4-Ether | 1,4-Diol |
|---|---|---|---|---|---|---|
| Dowex WX-8 Resin | 150 | 2.0 | 10.3 | 9.9 | 42.5 | 27.4 |
| Homogeneous H3PO4 | 95 | 3.0 | 2.5 | 2.3 | 70.4 | 22.6 |
| Homogeneous H2SO4 | 95 | 2.0 | 46.8 | 2.5 | 8.5 | 42.1 |
| NaH2PO4 | 170 | 1.0 | 3.3 | .7 | 95.3 | .7 |
| CaHPO4 | 175 | 1.0 | .1 | .6 | 91.7 | .5 |

TABLE I-continued

| Catalyst | Temp (°C.) | Time (h) | THF[a] | 1,4-Dicap[e] | 1,4-Ether | 1,4-Diol |
|---|---|---|---|---|---|---|
| Ca(H$_2$PO$_4$)$_2$ | 175 | 1.0 | 1.4 | 5.6 | 67.0 | 18.4 |
| HY Molecular Sieves[b] | 190 | 1.0 | 15.7 | 0.0 | 1.9 | 71.4 |
| Linde Sieve SK-41 | 175 | 1.0 | 1.5 | 0.0 | 56.1 | 30.7 |
| 10% H$_2$SO$_4$ Washed Al$_2$O$_3$[c] | 125 | 1.0 | .9 | 3.7 | 86.1 | 4.8 |
| 10% H$_3$PO$_4$ Washed Al$_2$O$_3$ | 95 | 1.0 | .7 | .4 | 94.1 | 1.7 |
| 30% H$_3$PO$_4$ Washed Al$_2$O$_3$ | 170 | 1.0 | 2.2 | 3.8 | 58.9 | 35.0 |
| 20 wt. % H$_3$PO$_4$ Impregnated Al$_2$O$_3$[d] | 170 | 1.0 | 1.0 | 2.4 | 80.3 | 16.3 |
| 10 wt. % H$_3$PO$_4$ Impregnated silicia-alumina | 150 | 1.0 | 1.7 | .2 | 6.6 | 87.0 |

[a]All data are in mole percent.
[b]NaY Sieve was ion exchanged with NH$_4$Cl and heated in a vacuum oven at 800° C.
[c]This catalyst was washed with an aqueous acid solution, filtered, and dried at 100° C. under vacuum overnight.
[d]This catalyst was prepared by dissolving a weighed amount of acid (1–2 g) in 100 ml distilled water and slurried with 10 g catalyst base. The water was removed by rotary evaporation to give dry catalyst. This was further dried in a vacuum oven overnight at 50–100° C.
[e]1,4-di-t-butoxybutane As is manifest from Table I, sulfuric acid blended with the feedstock provided the best combination of conversion rate (of the 1,4-ether) and selectivity (about a 1:1 product mix) at 95° C. Activated zeolites (see Table I, note b) and silica-alumina impregnated with H$_3$PO$_4$ exhibited high conversion rates but low rates of THF formation, behavior that appears to be consistent with acid catalyst behavior in the Chambers, et al. patent. The language in such prior art as U.S. Pat. No. 3,467,679—Rogers (column 1, lines 29–53) would have led to a contrary prediction. Further, phosphoric acid was found to deactivate rapidly in the present investigations.

The use of homogeneous acid catalysts in the preparation of a product from which the 1,4-diol is to be distilled necessitates the neutralization of the acid (as by the use of a basic resin or the addition of caustic) to avoid conversion of the diol to THF during the distillation step. Thus, the use of such a catalyst is more expensive both in requiring the added neutralization procedure and, because of the large consumption of catalyst.

Based upon the results from the tests shown in Table I it was decided to run a small scale continuous microplant apparatus using as the feedstock the product stream from a hydrogenation process in which 4-t-butoxy-n-butyraldehyde is reduced. The preparation of 4-t-butoxy-n-butyraldehyde is disclosed in U.S. Pat. No. 4,287,127—Harris, et al. and European Patent Application No. 18,163, both of which are incorporated by reference. Initially selected as catalysts for microplant tests were acid-impregnated silica-alumina (with sulfuric acid substituted for phosphoric acid), Amberlyst-15 acid ion-exchange resin, and Linde Sieve SK-41. Several tests were also conducted using untreated silica-alumina to provide a basis of comparison with the acid-treated material. It was expected that the acid-treated silica-alumina would outperform the untreated silica-alumina by a wide margin. As is established by the data, the untreated silica-alumina catalyst performed surprisingly well with operating parameters in a relatively narrow range of temperature and reactor residence time. This result was quite fortuitous, because plant operation with untreated silica-alumina catalyst is simpler and more economic than operation with acid-treated silica-alumina. Although acid loading can be altered in situ by washing the bed, operation must be interrupted for as much as 24 hours to conduct the catalyst bed wash. An additional problem is catalyst attrition, which occurs with acid-washed catalysts.

The catalyst material of this invention is used substantially as received, i.e. as it moves in commerce. Thus, with the exception of mechanical modification such as crushing and sieving to achieve some desired size pattern the SiO$_2$.Al$_2$O$_3$ is untreated.

Table II sets forth data obtained during microplant tests. The microplant apparatus was a vertically mounted ½″ stainless steel tube about 6 inches in length packed with 10 ml crushed and sieved (10–15 mesh) catalyst. This tube was connected by means of standard commercial fittings to ⅛″ feed and product lines. In these tests feed was pumped to the top of the bed, although flow in the reverse direction could have been used. Liquid and gaseous products were removed at the bottom. The entire apparatus was immersed in an oil bath. Products were cooled in a coil of tubing immersed in ice water and pumped to a vapor liquid separator. Liquid samples were analyzed by gas chromatography as described earlier. Feedstock composition was approximately 85% 4-t-butoxy-n-butanol and 15% 3-t-butoxy-2-methyl-n-propanol. Minor feedstock impurities (<0.5%) include 1,4-di-t-butoxy-n-butanol, 4-t-butoxy-n-butyraldehyde, 1,4-butanediol, 2-methyl-1,3-propanediol, 2′,6-di-t-butoxy-2-ethylhexanol and 2-(4′-t-butoxy-n-butoxy)tetrahydrofuran. All concentration designations are mole %.

TABLE II

| TEST | CATALYST | FLOW RATE (ml/hr) | TEMP (°C.) | CONVERSION[a] | SELECTIVITY[b] | RATE[c] | THF | 1,4-DICAP[d] | 1,3-ETHER[e] | 1,4-ETHER[f] | 1,3-DIOL[g] | 1,4-DIOL[h] |
|---|---|---|---|---|---|---|---|---|---|---|---|---|
| 1 | Amberlyst-15[j] | 40 | 100 | 74.0 | 41.0 | 18.0 | 26.0 | 3.7 | 4.9 | 17.2 | 10.6 | 37.5 |
| 2 | Amberlyst-15 | 40 | 110 | 91.0 | 64.0 | 22.0 | 43.7 | 2.2 | .70 | 5.8 | 23.2 | 24.1 |
| 3 | Linde Sieve SK-41[k] | 60 | 160 | 58.3 | 15.8 | 17.8 | 6.6 | 4.8 | 8.5 | 33.2 | 8.8 | 38.1 |
| 4 | Linde Sieve SK-41 | 60 | 180 | 73.4 | 16.5 | 22.4 | 9.9 | 2.2 | 6.4 | 22.7 | 8.5 | 50.2 |
| 5 | Linde Sieve SK-41 | 30 | 180 | 77.2 | 23.7 | 11.8 | 14.6 | 3.0 | 6.8 | 18.3 | 10.5 | 46.9 |
| 6 | Grace-Davison 980-25[i] | 40 | 160 | 97.0 | 15.9 | 19.8 | 12.9 | <.1 | .5 | 3.0 | 15.2 | 68.1 |

TABLE II-continued

| TEST | CATALYST | FLOW RATE (ml/hr) | TEMP (°C.) | CONVERSION[a] | SELECTIVITY[b] | RATE[c] | THF | 1,4-DICAP[d] | 1,3-ETHER[e] | 1,4-ETHER[f] | 1,3-DIOL[g] | 1,4-DIOL[h] |
|---|---|---|---|---|---|---|---|---|---|---|---|---|
| 7 | Grace-Davison 980-25 | 40 | 180 | 99.0 | 30.4 | 20.1 | 24.4 | <.1 | .7 | 1.3 | 17.7 | 55.8 |
| 8 | Grace-Davison 980-25 | 80 | 180 | 90.2 | 10.9 | 36.7 | 8.0 | 1.7 | 3.2 | 7.8 | 13.6 | 65.7 |
| 9 | Grace-Davison 980-25 | 40 | 200 | 96.4 | 70.1 | 19.6 | 53.7 | 1.1 | 1.5 | 2.4 | 18.3 | 22.9 |
| 10 | Grace-Davison 980-25 | 80 | 200 | 92.2 | 26.4 | 37.5 | 20.0 | 1.5 | 3.0 | 6.0 | 13.5 | 55.9 |
| 11 | 10 wt % H$_2$SO$_4$ on 980-25[m] | 40 | 180 | 98.4 | 57.5 | 20.0 | 47.4 | .4 | .0 | 1.2 | 15.9 | 35.1 |
| 12 | 10 wt % H$_2$SO$_4$ on 980-25 | 40 | 170 | 96.0 | 26.6 | 19.5 | 21.0 | 1.0 | .1 | 3.0 | 17.0 | 58.0 |
| 13 | 20 wt % H$_2$SO$_4$ on 980-25[m] | 40 | 160 | 89.7 | 28.9 | 18.2 | 22.0 | 1.8 | — | 8.5 | 12.9 | 54.6 |
| 14 | 20 wt % H$_2$SO$_4$ on 980-25 | 40 | 180 | 97.1 | 46.1 | 19.7 | 36.4 | .6 | — | 2.3 | 18.2 | 42.6 |
| 15 | 20 wt % H$_2$SO$_4$ on 980-25 | 60 | 180 | 94.3 | 23.0 | 28.7 | 18.5 | .9 | — | 4.8 | 14.0 | 61.8 |
| 16 | 20 wt % H$_2$SO$_4$ on 980-25 | 40 | 170 | 95.6 | 18.2 | 19.4 | 14.7 | .7 | — | 3.7 | 14.9 | 66.0 |
| 17 | 20 wt % H$_2$SO$_4$ on 980-25 | 30 | 170 | 97.7 | 27.8 | 14.9 | 22.7 | .4 | — | 1.9 | 16.2 | 58.9 |
| 18 | 20 wt % H$_2$SO$_4$ on 980-25 | 20 | 170 | 97.6 | 51.1 | 9.9 | 41.1 | 1.0 | — | 1.8 | 17.0 | 39.1 |
| 19 | 20 wt % H$_2$SO$_4$ on 980-25 | 20 | 165 | 98.3 | 34.6 | 10.0 | 27.7 | .4 | — | 1.3 | 18.3 | 52.3 |
| 20 | 20 wt % H$_2$SO$_4$ on 980-25 | 20 | 175 | 97.9 | 68.2 | 10.0 | 54.9 | 1.3 | — | .8 | 17.4 | 25.6 |

[a]All data are in mole percents; conversion is mole % THF + 1,3-DIOL + 1,4-DIOL.
[b]Selectivity is (THF/THF + 1,4-DIOL) × 100%.
[c]Rate is expressed in moles converted/liter of catalyst hour; the reactor contained 10.0 ml of catalyst.
[d]1,4-DICAP is 1,4-di-t-butoxy-n-butane
[e]1,3-ETHER is 2-methyl-3-t-butoxy-n-propanol
[f]1,4-ETHER is 4-t-butoxybutanol
[g]1,3-DIOL is 2-methyl-1,3-propanediol
[h]1,4-DIOL is 1,4-butanediol
[j]A polystyrene resin with sulfonic acid groups from Rohm & Haas. Approximately 4.5 meq/g.
[k]A synethetic zeolite in the acid form (HY zeolite).
[l]Silica-alumina catalyst - 75% SiO$_2$, 25% Al$_2$O$_3$.
[m]Prepared as described in note d from previous table.

Pressure parameters below 50 psi are not critical to the successful practice of this invention and this process can be carried out under widely varying pressures, e.g. sub-, super- or atmospheric pressures.

The solid acidic mixed oxide catalysts include any solid acidic silica-alumina composition, e.g. any solid acidic oxide mixture of silica and alumina, i.e. SiO$_2$.Al$_2$O$_3$. The oxides of silica and alumina can be present in any proportion. Illustratively, the weight percent of presently preferred SiO$_2$.Al$_2$O$_3$ mixed oxides are within the range of from about 90:10 to about 70:30.

Surface area parameters of the mixed oxides measured in square meters per gram (m$^2$/g) are not critical to the efficacy of the process. Generally effective SiO$_2$.Al$_2$O$_3$ surface areas are within the range of from about 50 to about 400 m$^2$/g.

| Grace-Davison - SiO$_2$.Al$_2$O$_3$ Typical Analysis | |
|---|---|
| | Grade 980-25 |
| CHEMICAL PROPERTIES | |
| (wt. %, Dry Basis @ 1750° F.) Total Volatile @ 1750° F. | 2.5 |
| Silica, SiO$_2$ | 74.5 |
| Alumina, Al$_2$O$_3$ | 25.0 |
| Sodium, Na$_2$O | 0.05 |
| Sulfate, SO$_4$ | 0.30 |
| Iron, Fe | 0.03 |
| Calcium, CaO | 0.05 |
| Chlorine, Cl | <.01 |
| PHYSICAL | |
| Surface Area, m$^2$/gm | 325. |
| Pore Volume, cc/gm | 0.45 |
| Packed Density, gm/cc | 0.73 |
| Avg. Crush Strength, lbs. | 15(3/16") |

These results (as well as the results of separate tests not shown here) establish that neither the Amberlyst nor the Linde catalyst (both acid catalysts) provides the requisite degree of control for a commercial process. Besides, the yield of THF with the Linde material was too low. Both of these materials would seem to be logical choices in view of the teachings in the Rogers patent and this behavior was unexpected.

The very fact that untreated silica-alumina catalyst provides high feedstock conversion, convenient predeterminable selectivity and rates of conversion comparable to the conversion, selectivity and conversion rates exhibited by acid washed silica-alumina (at comparable values of LHSV) without its disadvantages is surprising in itself. Although the overall useful temperature range for the practice of this invention can be from about 160°-200° C. and the LHSV can vary from about 2 to about 6 liter/liter catalyst/hr, the preferred operating parameters include temperatures (i.e. reactor tube wall temperature) in the 180°-200° C. range with LHSV in the 3-5 range. With temperatures below 180° C. the selectivity approaches a linear increase with temperature, but in the preferred temperature range the increase in selectivity is significantly greater than linear and yet is readily controllable for providing flexibility of coproduction in the range of 70:30 mole % to 30:70 mole % (1,4-diol to THF) of the 1,4-butanediol initially produced from the conversion of 4-t-butoxy-n-butanol. This deviation from linearity was unanticipated.

The 1,4-diol produced is useful in the preparation of polyesters, e.g. polybutylene terephthalates, and THF is a useful intermediate in the manufacture of certain chemicals and plastics.

What I claim as new and desire to secure by Letters Patent of the United States is:

1. A process for the coproduction of 1,4-butanediol and tetrahydrofuran comprising contacting solid acidic silica-alumina mixed oxide catalyst in a single reactor with a liquid feedstock composition containing at least about 70 mole % of 4-t-butoxy-n-butanol at operating temperatures in the range of 160° to 200° C. at a liquid hourly space velocity in the range of from about 2.0 to about 6.0 liter/liter catalyst/hr. to produce a mixture in said reactor in which the ultimate product of conversion of the 4-t-butoxy-n-butanol is 1,4-butanediol and tetrahydrofuran present in a preselected ratio in mole percent in the range of 7:3 to 3:7 of 1,4-butanediol to tetrahydrofuran.

2. The coproduction process of claim 1 wherein the operating temperature is in the range of 180° to 200° C.

3. The coproduction process of claim 2 wherein the liquid hourly space velocity is in the range of 3.0 to 5.0 liter/liter catalyst/hr.

4. The coproduction process of claim 1 wherein the conversion of 4-t-butoxy-n-butanol to 1,4-butanediol to tetrahydrofuran is in excess of 90 percent.

5. The coproduction process of claim 1 wherein the silica-alumina catalyst mixed oxides are in the compositional range of from about 90 weight % $SiO_2$:10 weight % $Al_2O_3$ to about 70 weight % $SiO_2$:30 weight % $Al_2O_3$.

6. The coproduction process of claim 1 wherein the operating pressure is less than 50 psi.

7. The coproduction process of claim 1 wherein the single reactor comprises a conventional reaction tube.

8. The coproduction process of claim 1 wherein the balance of the feedstock composition is made up substantially of 2-methyl-3-t-butoxy-n-propanol, which results in the formation of 2-methyl-1,3-propanediol and 2-methylpropene.

* * * * *